US00PP36482P2

(12) United States Plant Patent
Miyazaki

(10) Patent No.: US PP36,482 P2
(45) Date of Patent: Feb. 18, 2025

(54) ***SENECIO* PLANT NAMED 'Sene Toyonai'**

(50) Latin Name: *Senecio cruentus*
Varietal Denomination: Sene Toyonai

(71) Applicant: Kiyoshi Miyazaki, Shiga (JP)

(72) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 18/620,763

(22) Filed: Mar. 28, 2024

(51) Int. Cl.
*A01H 5/02* (2018.01)
*A01H 6/14* (2018.01)

(52) U.S. Cl.
USPC ..... Plt./480
CPC ..... *A01H 6/14* (2018.05)

(58) Field of Classification Search
USPC ..... Plt./480
CPC ..... A01H 6/14; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Senecio* plant named 'Sene Toyonai', characterized by its compact, upright and uniformly mounded plant habit; vigorous growth habit; freely branching habit; freely flowering habit; daisy-type inflorescences with ray florets that are dark violet in color and white towards the base forming a central ring; and good garden performance.

2 Drawing Sheets

Figure 1:
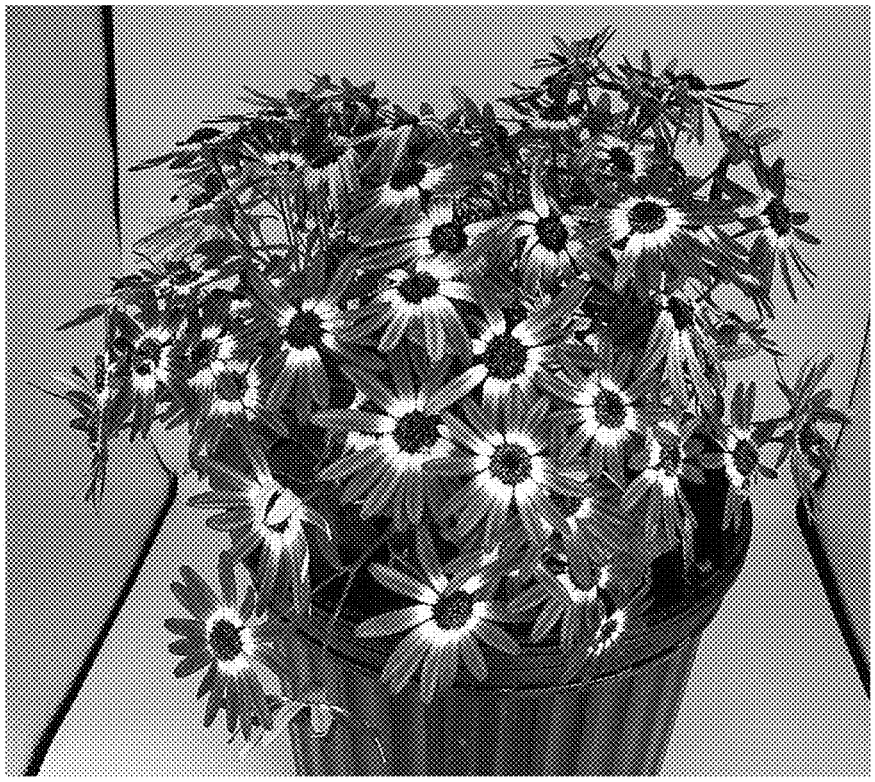

Botanical designation: *Senecio cruentus.*
Cultivar denomination: 'SENE TOYONAI'.

STATEMENT REGARDING PRIOR DISCLOSURES BY THE INVENTOR/APPLICANT & ASSIGNEE

The Inventor/Applicant and Assignee, Suntory Flowers Limited of Tokyo, Japan, assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102 (b) (1) for disclosure and/or sales prior to the filing date but less than one year prior to the effective filing date.

BACKGROUND OF THE INVENTION

The present invention relates to a new and distinct cultivar of *Senecio* plant, botanically known as *Senecio cruentus,* and hereinafter referred to by the name 'Sene Toyonai'.

The new *Senecio* plant is a product of a planned breeding program conducted by the Inventor in Higashiomi, Shiga, Japan. The objective of the breeding program is to create new compact, upright and uniformly mounding *Senecio* plants with a freely-branching habit and numerous attractive inflorescences.

The new *Senecio* plant originated from a cross-pollination conducted by the Inventor in March 2014 of a proprietary selection of *Senecio cruentus* identified as code designation 08-125-3, not patented, as the female, or seed, parent with a proprietary selection of *Senecio cruentus* identified as code designation S12-78-Tb1, not patented, as the male, or pollen, parent. The new *Senecio* plant was discovered and selected by the Inventor as a single flowering plant within the progeny of the stated cross-pollination in a controlled greenhouse environment in Higashiomi, Shiga, Japan in February 2015.

Asexual reproduction of the new *Senecio* plant by terminal vegetative cuttings in a controlled greenhouse environment in Higashiomi, Shiga, Japan since October 2016 has shown that the unique features of this new *Senecio* plant are stable and reproduced true to type in successive generations.

SUMMARY OF THE INVENTION

Plants of the new *Senecio* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sene Toyonai'. These characteristics in combination distinguish 'Sene Toyonai' as a new and distinct *Senecio* plant:

1. Compact, upright and uniformly mounded plant habit.
2. Vigorous growth habit.
3. Freely branching habit.
4. Freely flowering habit.
5. Daisy-type inflorescences with ray florets that are dark violet in color and white towards the base forming a central ring.
6. Good garden performance.

Plants of the new *Senecio* can be compared to plants of the female parent selection. Plants of the new *Senecio* differ primarily from plants of the female parent selection in ray floret color as ray florets of plants of the new *Senecio* are dark violet in color and white towards the base whereas ray florets of plants of the female parent selection are solid blue in color.

Plants of the new *Senecio* can be compared to plants of the male parent selection. Plants of the new *Senecio* differ primarily from plants of the male parent selection in ray floret color as ray florets of plants of the new *Senecio* are dark violet in color and white towards the base whereas ray florets of plants of the male parent selection are solid white in color.

Plants of the new *Senecio* can also be compared to plants of *Senecio cruentus* X *Senecio heritieri* 'Sunsenelibubi', disclosed in U.S. Plant Pat. No. 20,191. In side-by-side comparisons, plants of the new *Senecio* differ from plants of 'Sunsenelibubi' in the following characteristics:

1. Plants of the new *Senecio* are more compact than plants of 'Sunsenelibubi'.
2. Plants of the new *Senecio* are not as freely branching as plants of 'Sunsenelibubi'.
3. Plants of the new *Senecio* are more freely flowering than plants of 'Sunsenelibubi'.
4. Plants of the new *Senecio* differ from plants of 'Sunsenelibubi' in ray floret color as ray florets of plants of the new *Senecio* are dark violet in color and white towards the base whereas ray florets of plants of 'Sunsenelibubi' are lighter violet in color and white towards the base.

BRIEF DESCRIPTION OF THE PHOTOGRAPHS

The accompanying photographs illustrate the overall appearance of the new *Senecio* plant showing the colors as true as it is reasonably possible to obtain in colored reproductions of this type. Colors in the photographs may differ slightly from the color values cited in the detailed botanical description which accurately describe the colors of the new *Senecio* plant.

The photograph on the first photographic sheet FIG. 1 is a side perspective view of a typical flowering plant of 'Sene Toyonai' grown in a container.

Figure 2:
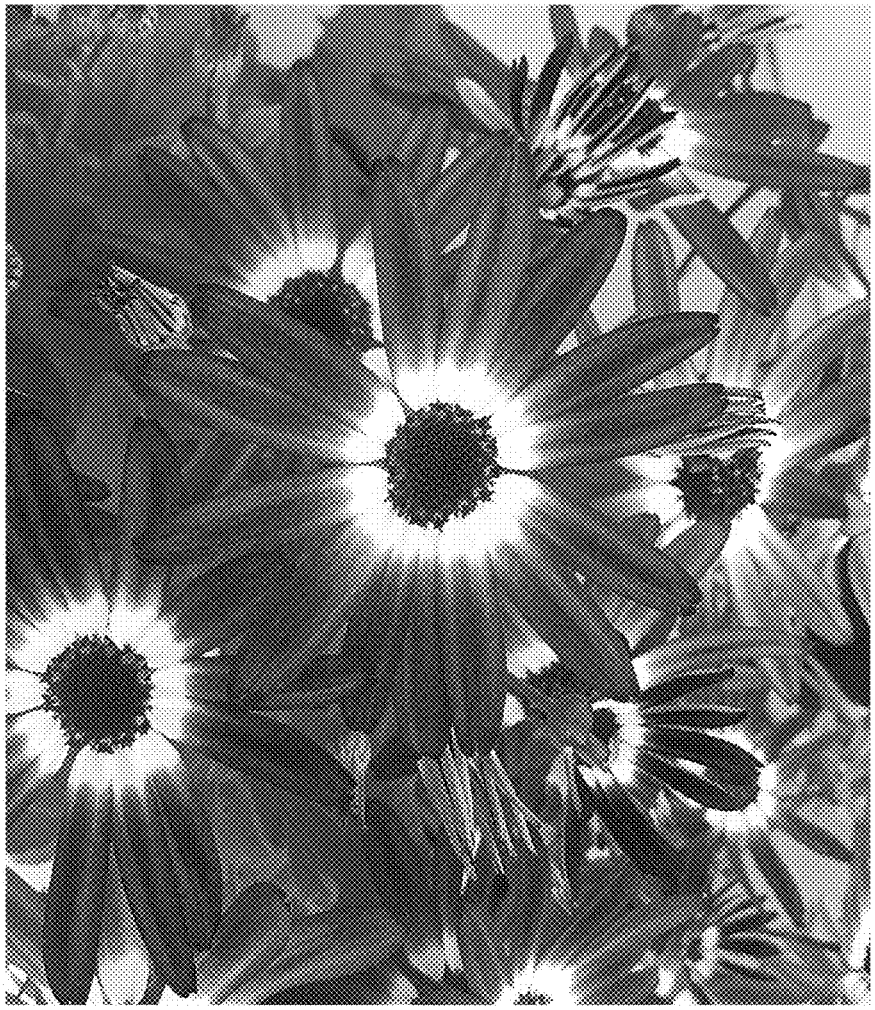

The photograph on the second photographic sheet FIG. 2 is a close-up view of typical inflorescences of 'Sene Toyonai'.

DETAILED BOTANICAL DESCRIPTION

The aforementioned photographs, following observations and measurements describe plants grown during the late winter/early spring in 24-cm containers in an outdoor nursery in Higashiomi, Shiga, Japan and under cultural practices typical of commercial *Senecio* production. During the production of the plants, day temperatures averaged 10° C. and night temperatures averaged 5° C. Measurements and numerical values represent averages for typical flowering plants. Plants were six months old when the photographs and the detailed description were taken. In the following description, color references are made to The Royal Horticultural Society Colour Chart, 2015 Edition, except where general terms of ordinary dictionary significance are used.

Botanical classification: *Senecio cruentus* 'Sene Toyonai'.

Parentage:

*Female, or seed, parent*.—Proprietary selection of *Senecio cruentus* identified as code designation 08-125-3, not patented.

*Male, or pollen, parent*.—Proprietary selection of *Senecio cruentus* identified as code designation S12-78-Tb1, not patented.

Propagation:

*Type*.—Terminal vegetative cuttings.

*Time to initiate roots, summer and winter*.—About one week at temperatures about 18° C. to 20° C.

*Time to produce a rooted young plant, summer and winter*.—About four weeks at temperatures about 18° C. to 20° C.

*Root description*.—Fine, fibrous; typically white in color; actual color of the roots is dependent on substrate composition, water quality, fertilizer type and formulation, substrate temperature and physiological age of roots.

*Rooting habit*.—Freely branching, dense.

Plant description:

*Plant form and growth habit*.—Compact, upright and uniformly mounded plant habit; daisy-type inflorescences positioned above the foliar plane; vigorous growth habit; freely branching habit with about five primary branches each with numerous secondary branches.

*Plant height*.—About 24.5 cm.

*Plant diameter*.—About 33.5 cm.

*Lateral branches*.—Length: About 14.6 cm. Diameter: About 2.5 mm. Internode length: About 2.3 cm. Strength: Strong. Aspect: Upright to somewhat outwardly. Texture: Sparsely pubescent. Color: Close to 138B.

*Leaf description*.—Arrangement: Alternate, simple. Length: About 5.2 cm. Width: About 6.4 cm. Shape: Cordate. Apex: Acute. Base: Cordate. Margin: Serrate to crenate with shallow indentations; slightly undulate. Texture and luster, upper surface: Sparsely pubescent, rough; matte. Texture and luster, lower surface: Densely pubescent; rough; matte. Venation pattern: Pinnate; reticulate. Color: Developing leaves, upper surface: Close to 137B. Developing leaves, lower surface: Close to 138C. Fully expanded leaves, upper surface: Close to 137C; venation, close to 138B. Fully expanded leaves, lower surface: Close to 138C; venation, close to 138C. Leaf petioles: Length: About 4.4 cm. Diameter: About 2 mm. Texture, upper and lower surfaces: Pubescent, rough. Color, upper and lower surfaces: Close to 138C.

Inflorescence description:

*Appearance*.—Daisy-type inflorescences with linear-shaped ray florets; inflorescences arising from upper leaf axils and positioned above the foliar plane on strong peduncles; disc and ray florets developing acropetally on a capitulum; inflorescences face mostly upright to outwardly; freely flowering habit with about 74 inflorescences developing per plant during the flowering season.

*Fragrance*.—None detected.

*Natural flowering season*.—Plants of the new *Senecio* begin flowering about 22 weeks after planting; plants flower continuously from winter to late spring in Japan; inflorescences maintain good substance for about two weeks on the plant; inflorescences persistent.

*Inflorescence buds*.—Height: About 1.8 cm. Diameter: About 7.3 mm. Shape: Globose. Color: Close to 91A.

*Inflorescence size*.—Diameter: About 6.4 cm. Depth (height): About 9 mm. Disc diameter: About 1.1 cm.

*Receptacles*.—Diameter: About 5.4 mm. Height: About 1.9 mm. Color: Close to 146C.

*Ray florets*.—Quantity and arrangement: About 14 per inflorescence arranged in a single whorl. Length: About 3 cm. Width: About 6 mm. Shape: Linear.

Apex: Rounded acute; occasionally, emarginate. Base: Attenuate. Margin: Entire, not undulate. Aspect: Initially upright, then horizontal; flat. Texture, upper and lower surfaces: Smooth, glabrous. Color: When opening, upper surface: Close to N89B; towards the base, close to NN155D. When opening, lower surface: Close to 91B. Fully opened, upper surface: Close to N89B; towards the base, close to NN155D; venation, similar to lamina colors; main color becoming closer to N89D with subsequent development. Fully opened, lower surface: Close to 91C; venation, close to 91C; color does not change with subsequent development.

*Disc florets*.—Quantity per inflorescence: About 143. Length: About 6.3 mm. Diameter, at apex: About 2 mm. Diameter, at base: About 1 mm. Shape: Tubular; apex dentate, five-pointed. Texture: Smooth, glabrous. Color, immature and mature: Close to N89A.

*Phyllaries*.—Quantity and arrangement: About twelve per inflorescence arranged in a single whorl forming a cylindrical involucre. Length: About 1.5 mm. Width: About 1.4 mm. Shape: Lanceolate; moderately recurved. Apex: Narrowly acute. Base: Fused. Margin: Entire. Texture, upper and lower surfaces: Smooth, glabrous. Color, inner surface: Close to 138A. Color, outer surface: Close to 138B.

*Peduncles*.—Length: About 4 mm. Diameter: About 1.4 mm. Strength: Strong. Aspect: Upright to outwardly. Texture: Sightly pubescent. Color: Close to 138A.

*Reproductive organs*.—Androecium: Present on disc florets only. Filament length: About 2.5 mm. Filament color: Close to 150D. Anther size: About 1 mm by 1.5 mm. Anther shape: Narrowly ellipsoidal. Anther color: Close to N89B. Pollen amount: Moderate. Pollen color: Close to 7C. Gynoecium: Present on both ray and disc florets. Pistil length: About 5.2 mm. Stigma shape: Bi-parted. Stigma color: Close to N89B. Style color: Close to 150C. Ovary color: Close to 144C.

*Seeds and fruits*.—To date, seed and fruit development have not been observed on plants of the new *Senecio*.

Pathogen & pest resistance: To date, plants of the new *Senecio* have not been observed to be resistant to pathogens and pests common to *Senecio* plants.

Garden performance & temperature tolerance: Plants of the new *Senecio* have good garden performance and have been observed to tolerate temperatures ranging from about 0° C. to about 30° C.

It is claimed:

1. A new and distinct *Senecio* plant named 'Sene Toyonai' as illustrated and described.

* * * * *